(12) United States Patent
Kadam et al.

(10) Patent No.: US 7,678,928 B2
(45) Date of Patent: Mar. 16, 2010

(54) PROCESS FOR MANUFACTURE OF SIMVASTATIN

(75) Inventors: Subhash Rajaram Kadam, Thane (IN); Mahendra Raghunath Patil, Thane (IN); Madhukar Shaligram Patil, Thane (IN); Sachin Arun Sasane, Thane (IN)

(73) Assignee: Lupin Limited, Mumbai (IN)

( * ) Notice: Subject to any disclaimer, the term of this patent is extended or adjusted under 35 U.S.C. 154(b) by 410 days.

(21) Appl. No.: 11/815,322

(22) PCT Filed: Jun. 17, 2005

(86) PCT No.: PCT/IN2005/000208

§ 371 (c)(1),
(2), (4) Date: Aug. 2, 2007

(87) PCT Pub. No.: WO2006/082594

PCT Pub. Date: Aug. 10, 2006

(65) Prior Publication Data

US 2008/0214843 A1 Sep. 4, 2008

(30) Foreign Application Priority Data

Feb. 4, 2005 (IN) .................. 116/MUM/2005

(51) Int. Cl.
*C07D 309/30* (2006.01)
(52) U.S. Cl. .................................... 549/292
(58) Field of Classification Search .................. 549/292
See application file for complete search history.

(56) References Cited

U.S. PATENT DOCUMENTS 6,562,984 B2 * 5/2003 Peters et al. ............... 549/292
2002/0147351 A1 10/2002 Peters et al.

FOREIGN PATENT DOCUMENTS

| EP | 1 110 959 A1 | 6/2001 |
| WO | WO 01/30773 A2 | 5/2001 |
| WO | PCT/IN04/000075 | 10/2005 |
| WO | WO 2005/095374 A1 | 10/2005 |

* cited by examiner

*Primary Examiner*—D. Margaret Seaman
*Assistant Examiner*—Nizal S Chandrakumar
(74) *Attorney, Agent, or Firm*—Merchant & Gould P.C.

(57) ABSTRACT

An improved method for manufacture of simvastatin of formula (I) in high purity. The process for preparation of compound (I) comprises

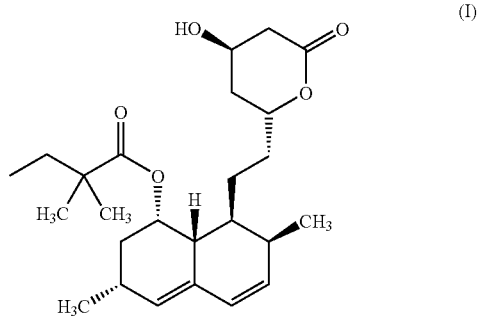
(I)

the steps of agitating a compound of formula (II),

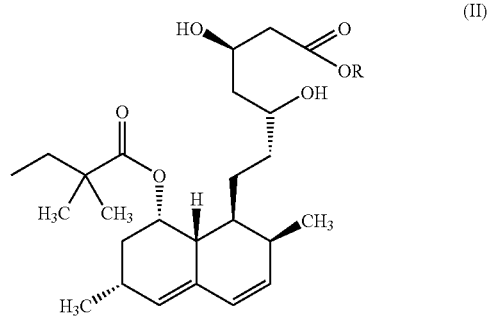
(II)

wherein R is hydrogen, $NH_4^+$ or an alkali metal in an organic solvent and in an inert atmosphere at a temperature of between 27° C. to 40° C. in the presence of a weak acid followed by neutralization with an organic base and obtaining compound of formula (I) in high purity and substantially free of impurities through a step of isolation and crystallization.

10 Claims, No Drawings

PROCESS FOR MANUFACTURE OF SIMVASTATIN

FIELD OF THE INVENTION

The present invention relates to an improved method for manufacture of simvastatin of formula (I) in high purity.

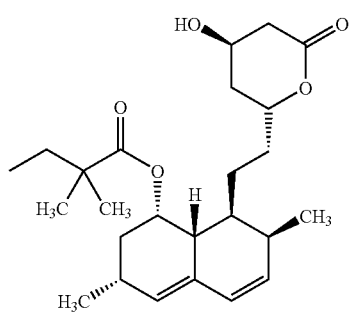
(I)

BACKGROUND OF THE INVENTION

Simvastatin of formula (I) is a valuable hypocholesteremic drug, which inhibits biosynthesis of cholesterol by competitively inhibiting 3-hydroxy-3-methylglutaryl-coenzyme A reductase (HMG-CoA reductase) thereby reducing the rate of formation of cholesterol in the human body. Simvastatin of formula (I) like its structurally similar analog lovastatin is active physiologically in the dihydroxylic acid form of formula (II) but is administered in the lactone form of formula (I).

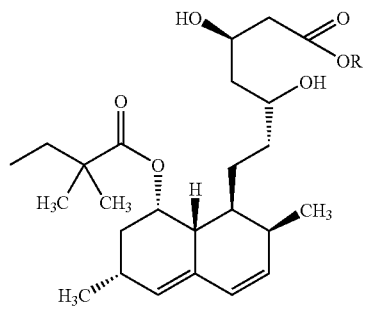
(II)

wherein R is hydrogen, $NH_4^+$ or an alkali metal

The lactone form (I) is prepared by lactonization of the 3,5-dihydroxy acid derivative of formula (II) lactonization by various methods, which generally involves heating compound of formula (II) in the presence or absence of a bronsted acid or a dehydrating agent at various temperatures, employing various solvents.

Lactonization of the 3,5-dihydroxy pentanoic acid derivative of formula (II) is invariably accompanied by the formation of associated impurities especially the dimer impurity of formula (III) in variable amounts. This impurity is usually formed at higher temperature or in highly acidic conditions. Another impurity encountered during lactonization is the anhydro impurity of formula (IV), which is formed in highly acidic conditions. These impurities are difficult to remove utilizing conventional methods of purification and if removed, considerably lower the yield of the product.

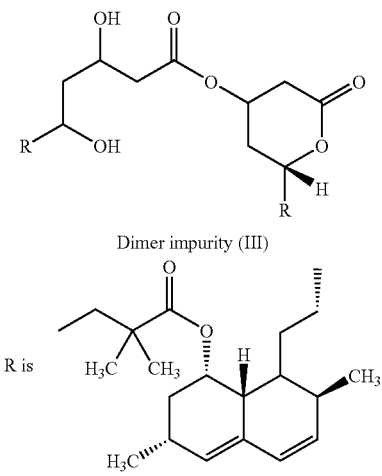

Dimer impurity (III)

R is 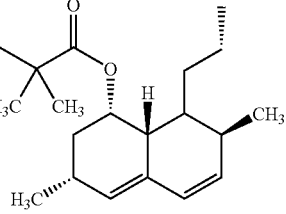

Prior art methods usually disclose the yield and purity of compound (I) but fail to mention any associated impurity such as the anhydro impurity of formula (IV) and the acetyl impurity (V), which could be formed during the reaction, when strong acids like methane sulfonic acid or a solvent like acetic acid is employed.

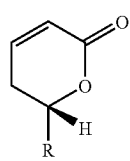
(IV)

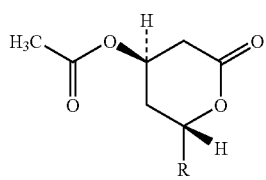
(V)

wherein R is

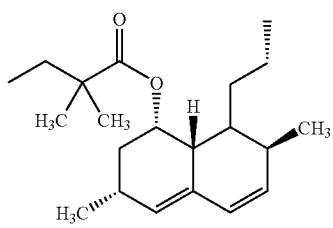

The minimization of the dimer impurity (III) is generally achieved by carrying out lactonization in a short duration or at a lower temperature or with dehydrating reagents like phosphorous pentoxide, molecular sieves etc which do not take part in the reaction.

The dimer impurity (III) is normally formed in reaction conditions, which are highly acidic or in concentrated solutions wherein there is a greater interaction between the substrate molecules. Therefore, prior art methods generally utilize high level of dilution of organic solvents between 40-50 times (w/w) per gram of the starting compound of formula (II) for controlling the level of impurities but in the process lactonization takes a longer time, between 20-60 hours for completion of reaction which consequently reduces the production capacity and increases the time cycle for each run.

Regulatory authorities all over the world are becoming very stringent about the level of impurities in an approved drug. Pharmacopoeial specification requires that the impurities such as the dimer impurity (III), anhydro impurity (IV) and acetyl impurity (V) in Simvastatin (I), which is difficult to remove by conventional methods, should be below 0.4%.

Needless to mention, most of the prior art methods do not give product conforming to the above mentioned criteria.

A brief summary of the prior art methods and their shortcomings has been already disclosed in our pending PCT Application PCT/IN04/00075, which describes an improved method for preparation of various compounds, which are structural analogues of simvastatin (I).

The method disclosed in PCT Application PCT/IN04/00075 is an improvement over the prior art methods and the invention residing in this application lies in the selection of a mixture of organic solvents viz. toluene and methyl ethyl ketone, temperature between 60-75° C., selection of catalyst, lower dilution of solvent which reduces reaction time and gives simvastatin of formula (I) of high purity, substantially free from impurities and conforming to pharmacopoeial specification.

The method disclosed in PCT Application PCT/IN04/00075 however requires a higher temperature (60-75° C.), a mixture of solvents viz. toluene and methyl ketone in a specific ratio (7:3). Further, Simvastatin (I) obtained by the above method also requires extensive purification for removal of associated impurities, since the dimer impurity (III) and the anhydro impurity (IV) (0.40% and 0.64% respectively) formed during lactonization are sufficiently high. Purification for removal of impurities lowers the yield to between 65-72%, therefore it is imperative to control these impurities during lactonization itself.

Therefore there exists a need for a method for manufacture of simvastatin of formula (I), which is simple, efficient and cost-effective but also gives simvastatin (I) in high yield and purity, substantially free of impurities.

It is therefore an object of the present invention to provide an improved process for preparation of simvastatin of formula (I) of high purity, with better yields and dimer purity (III) less than 0.05% and anhydro impurity of formula (IV) at less than 0.15%.

Another object of the invention is to provide an improved process for synthesis of simvastatin of formula (I) by agitating the corresponding 3,5-dihydroxy pentanoic acid derivative of formula (II) in a chlorinated solvent and in the presence of a weak acid like orthophosphoric acid at a temperature between 27-40° C. and in a short duration of 12-14 hours as compared to between 20-60 hours reported in prior art methods.

Yet another object of the invention relates to carrying out lactonization of the compound of formula (II) in a significantly lower dilution between 17 to 20 times (w/w) per gram of compound (II) and to give compound (I) of high purity and thereby making the process cost-effective.

It is a yet further object of the present invention to reduce the number of steps for isolating simvastatin (I) so as to conform to pharmacopoeial specification.

The present inventors have found that simvastatin of formula (I) can be synthesized from the 3,5-dihydroxy pentanoic acid derivative or its salt (II) by agitating in a chlorinated solvent for a period of 12-14 hours in the presence of a weak acid like orthophosphoric acid to give compound (I) of high purity, with dimer impurity (III) between 0.02% to 0.04% and which conforms to pharmacopoeial specification.

The present inventors further found that lactonization of compound of formula (II) can be achieved in a higher yield and purity through a method which utilizes a single solvent like a chlorinated solvent, at a lower temperature of 35±2° C. and utilizing an aqueous solution of an inorganic acid like orthophosphoric acid which not only reduces the dimer impurity of formula (III) below 0.05% but also reduces the formation of the anhydro impurity (IV) below 0.15%, during the lactonization reaction. Due to the low level of impurities formed during the reaction, extensive purification like prior art methods are not required thereby improving the yields.

SUMMARY OF THE INVENTION

According to the main aspect of the present invention there is provided an improved process for preparation of compound (I)

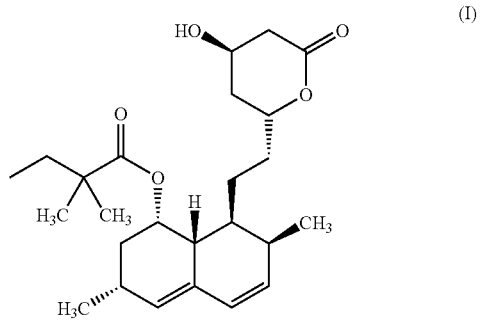

comprising the steps of agitating a compound of formula (II),

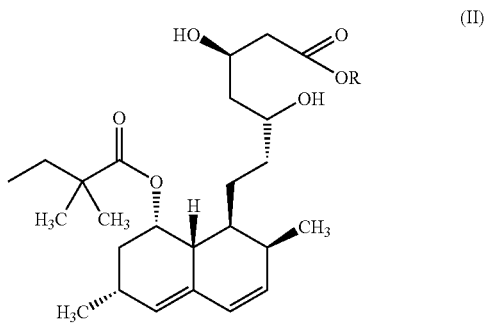

wherein R is hydrogen, $NH_4^+$ or an alkali metal in an organic solvent and in an inert atmosphere at a temperature of between 27° C. to 40° C. in the presence of a weak acid followed by neutralization with an organic base and obtaining compound of formula (I) in high purity ad substantially free of impurities through a step of isolation and crystallization.

One aspect of the invention provides a simple, efficient, cost-effective method for manufacture of simvastatin of formula (I) of high purity substantially free from impurities.

Another aspect of the invention provides a method for manufacture of simvastatin of formula (I) by agitating the corresponding 3,5-dihydroxy pentanoic acid derivative or its salt of formula (II) in a chlorinated solvent, at a temperature of 27° C.-40° C.

Yet a further aspect of the invention relates to a method for carrying out the lactonization in a very low dilution of solvent 17 to 20 times (w/w) per gram of compound (II) at a temperature of 27° C.-40° C. in a short time of 12-14 hours, followed by neutralization with an organic base, evaporation of the solvent, addition of an hydrophobic solvent and an organic base, refluxing the mixture and isolating the product of formula (I).

Yet another aspect of the invention relates to a method for purification of compound (I) by recrystallization of compound (I) from a mixture of a water-miscible solvent and water to give compound of high purity, having dimer impurity (III) less than 0.05%, anhydro impurity (IV) less than 0.15% and conforming to pharmocopoeial specifications.

DETAILED DESCRIPTION OF THE INVENTION

More particularly simvastatin of formula (I) can be synthesized in a higher yield and purity with fewer steps of purification comprising agitating a 3,5-dihydroxy pentanoic acid derivative of formula (II) in an chlorinated solvent at a lower temperature in the range of 27-40° C. which gives the compound of formula (I)
  a) in higher yield (82-86%),
  b) of high purity (99.5-99.8%),
  c) substantially free from the dimer impurity (III; 0.02-0.04) and anhydro impurity (IV; 0.10-0.13%). There is no possibility of forming the acetyl impurity (V) since the present method does not utilize acetic acid as solvent during the reaction, It is to be noted that by this method the number of steps for isolating simvastatin (I) conforming to pharmacopoeial specification are less as compared to prior art methods primarily due to control of impurity formation during the lactonization reaction as a result of which additional steps of purification are not required.

Prior art methods on the other hand have a substantial increase in the number of operations due to the formation of associated impurities at the reaction stage.

The method embodied herein is a selection of solvent and reaction temperature as a result of which a better conversion of product is obtained with minimal formation of impurities and this has contributed considerably in reducing the cost of manufacture.

The selection of the solvent, reaction temperature and carrying out the reaction in the presence of a weak acid like orthophosphoric acid for minimization of associated impurities like dimer impurity (III) below 0.05% and anhydro impurity below 0.15% during the reaction and to provide simvastatin of formula (I) with better yields and high purity, forms the basis of the invention.

The method of manufacture of simvastatin of formula (I) as per the present invention is summarized in Scheme-I for ready reference.

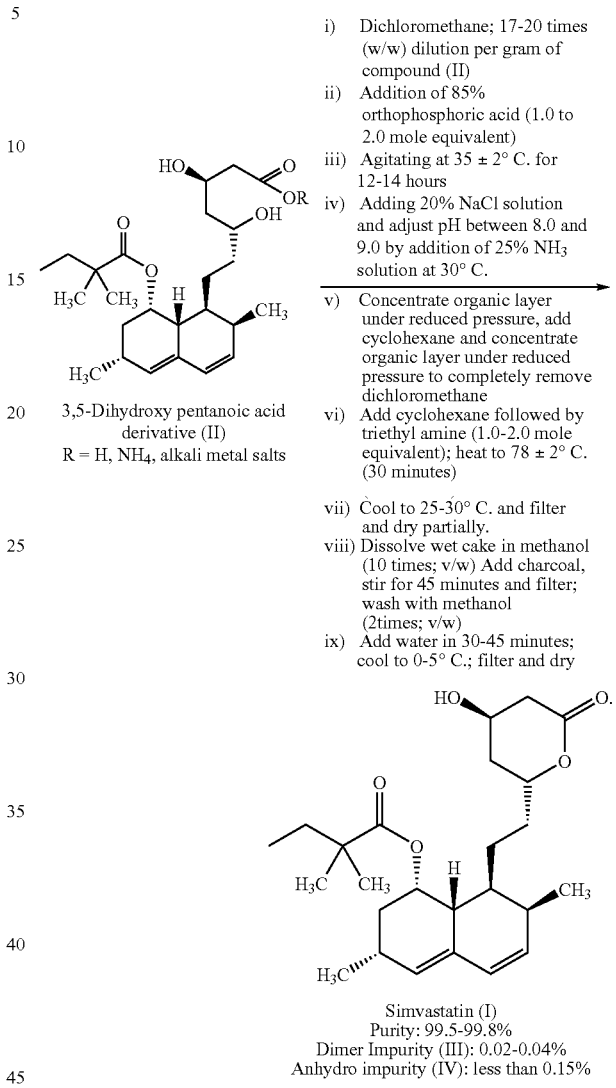

Scheme-I: Method for preparation of simvastatin of formulas (I) as described in the present invention.

The superiority of the present method over the method disclosed in PCT Application PCT/IN04/00075 is evident from Table-I which gives a comparison of the amount of the dimer impurity (III) and the anhydro impurity (IV) formed by the above two methods.

TABLE I

Comparison of simvastatin obtained by the methods disclosed in the present invention and that obtained by the method disclosed in the pending PCT Application PCT/IN04/00075 in terms of yield, purity and level of impurities.

| No. | | Simvastatin (I) obtained by the method disclosed in the present invention. | Simvastatin (I) obtained by the method disclosed in pending PCT Application PCT/IN04/00075 |
|---|---|---|---|
| 1. | Product conversion | Between 93 to 96% | Between 92 to 93% |

TABLE I-continued

Comparison of simvastatin obtained by the methods disclosed in the present invention and that obtained by the method disclosed in the pending PCT Application PCT/IN04/00075 in terms of yield, purity and level of impurities.

| No. | | Simvastatin (I) obtained by the method disclosed in the present invention. | Simvastatin (I) obtained by the method disclosed in pending PCT Application PCT/IN04/00075 |
|---|---|---|---|
| 2. | Dimer impurity (III) formed during reaction | Between 0.02-0.04% | 0.35-0.40% |
| 3. | Anhydro impurity (IV) formed during reaction. | Between 0.10-0.13% | 0.5-0.6% |
| 4. | Isolated yield | 82-86% | 65-72% |

A. Lactonisation of Corresponding 3,5-Dihydroxy Derivative of Formula (II).

The lactonization of the corresponding 3,5-dihydroxy pentanoic acid derivative of formula (II) to give simvastatin of formula (I) was found to depend on the following parameters:
 a) selection of solvent, and
 b) effect of reaction temperature.

a) Selection of Solvent:

Several solvents selected from chlorinated solvents such as dichloromethane, chloroform and ethylene dichloride and alkyl acetates such as ethyl acetate, ketones such as methyl ethyl ketone, hydrocarbons such as toluene or a mixture of a hydrocarbon and a ketone such as a (7:3) mixture of toluene and methyl ethyl ketone as disclosed in our pending PCT Application No. PCT/IN04/00075 were tried out.

The results obtained utilizing the above solvents with respect to the amount of associated impurities formed are summarized in Table-II.

TABLE II

Comparison of various solvents tried out for preparation of Simvastatin (I) and their effect on the formation of associated impurities.

| No. | Solvents/s utilized for lactonization of compound of formula (II) | Dimer impurity (%) (III) | Anhydro impurity (%) (IV) | Total impurities formed during lactonization |
|---|---|---|---|---|
| 1. | Dichloromethane | 0.014% | 0.14% | 1.05% |
| 2. | Chloroform | 0.10% | 0.36% | 12.82% (inclusive of unknown impurity) |
| 3. | Dichloroethane | 0.10% | 0.24% | 5.35% (inclusive of unknown impurity) |
| 4. | Ethyl acetate | 0.39% | 0.56% | 1.26% |
| 5. | Methyl ethyl ketone | 0.10% | 0.32% | 21.45% (inclusive of unknown impurity) |
| 6. | Toluene | 0.49% | 0.32% | 1.42% |
| 7. | Methyl ethyl ketone and toluene mixture (7:3) | 0.185% | 0.45% | 1.63% |

Inference: Dichloromethane gives the best results in terms of reducing impurities in identical conditions.

It is evident from the above data that among all the above solvents/solvent mixture, dichloromethane was found to be better, as impurity formation was minimized resulting in higher conversion.

It should be noted here that utilization of dichloromethane for preparation of simvastatin (I) has also been reported in U.S. Pat. No. 6,562,984 B2, but the method embodied in the present invention is far superior in terms of yield, minimization of impurities and reduction in the number of purification steps for obtaining simvastatin of formula (I).

U.S. Pat. No. 6,562,984 B2 discloses a method in which simvastatin (I) is prepared by lactonization of compound (II) in the presence of a anhydrous lactonizing agent like methanesulfonic acid and employing a solvent like dichloromethane at ambient temperature. This patent also discloses that the yield of simvastatin (I) is only 64%, which is far below the yield (82-86%) obtained by the method embodied in this application.

Further, U.S. Pat. No. 6,562,984 B2 discloses that the content of the dimer impurity (III) is below 0.1% but does not mention other associated impurities especially the anhydro impurity (IV), which is usually formed when a strong acid like methanesulfonic acid is employed.

Replication of the method disclosed in Example 1 of U.S. Pat. No. 6,562,984 B2 indeed showed that the anhydro impurity [IV; 0.60%] was formed. It was not surprising to find that the simvastatin (I) thus obtained had to be purified twice utilizing ethanol/water combination to obtain simvastatin (I) conforming to pharmacopoeial specification.

The lower level of anhydro impurity (0.13%) obtained by the method embodied herein is due to presence of a weak acid like orthophosphoric acid (pka: +2.15) which controls the anhydro impurity below (0.15%) as compared to methanesulfonic acid (pka: −2.0), which is a much stronger acid.

Further, the present method is more versatile as it does not require anhydrous conditions for lactonization as compared to U.S. Pat. No. 6,562,984 B2, which requires anhydrous reaction conditions in addition to an anhydrous lactonizing agent.

It should be noted that there is a substantial increase in the number of steps in the method disclosed in U.S. Pat. No. 6,562,984 B2 as compared to the present method, primarily due to substantial formation of the anhydro impurity (IV) during the reaction.

b) Effect of Reaction Temperature:

The present inventors have found that the time required for completion of lactonization is dependent on the reaction temperature also.

The reaction was carried out in various temperature ranges between 25° C. and 40° C., it was found that at lower temperature between 27-30° C. lactonization required almost double the time i.e. nearly 26 hours for the reaction to go to completion, which increased the time cycle for each run. As the temperature was increased above 30° C., the reaction was faster and lactonization was completed in 12-14 hours.

The impact of temperature on the rate of the reaction and formation of associated impurities is given in Table-III.

TABLE III

Comparison of rate of reaction at different temperatures and effect on the formation of associated impurities.

| No. | Reaction temperature | Reaction time | Dimer + Anhydro impurity | Total impurity |
|---|---|---|---|---|
| 1. | 27-30° C. | 26 hours | 0.20 + 0.05 | 0.45 |
| 2. | 33-35° C. | 14 hours | 0.02 + 0.13 | 0.26 |
| 3. | 35-37° C. | 14 hours | 0.02 + 0.13 | 0.25 |
| 4. | 37-40° C. | 14 hours | 0.03 + 0.15 | 0.30 |

From the above it is evident that the rate of lactonization is slow at lower temperature (27° C.-30° C.) while at higher temperature (33° C.-40° C.) the reaction is fast and is completed in almost half the time without affecting the impurity profile of the reaction.

There is absence of any significant rise in impurity formation particularly the dimer (III) and the anhydro impurity (IV) even after agitating for 26 hours at 27-30° C. This is due to the presence of a weak acid like orthophosphoric acid in the reaction mixture. The presence of a strong acid like methanesulfonic acid utilized in U.S. Pat. No. 6,562,984 B2 would have definitely increased the impurity level particularly the anhydro impurity (IV).

Orthophosphoric acid is employed in molar proportions of between 1.1 to 2.5 moles per mole of the 3,5-dihydroxy pentanoic acid intermediate but preferably between 1.10 and 1.50 moles per mole of compound (II).

B. Isolation and Purification of Simvastatin of Formula (I).

After completion of reaction, the highly acidic reaction medium (pH: 1.5) was neutralised with aqueous ammonia between pH 8.0 to 9.0. The organic layer containing simvastatin was concentrated to completely remove dichloromethane. Cyclohexane [(5 times volume per gram of compound (II)] was added to the concentrated residue and distilled under reduced pressure to completely remove dichloromethane.

Cyclohexane [(5 times volume per gram of compound (II)] was again added to the concentrated residue followed by addition of an organic base preferably triethyl amine [1.0 mole equivalent per mole of compound (II)] was added to the mixture and refluxed for 30-40 minutes at 78±2° C. to completely neutralize traces of orthophosphoric acid and other acidic impurities. The reaction mixture is cooled to 10-15° C., filtered and washed with cyclohexane. The wet cake is utilized as such for removal of inorganic impurities by crystallization from a mixture of an alkanol and water.

Simvastatin of formula (I) is dissolved in a water-miscible solvent selected from alkanol and a ketone but preferably an alkanol.

The alkanol is selected from methanol, ethanol, n-propanol, isopropanol but preferably methanol.

Simvastatin of formula (I) is dissolved in methanol. The quantity of methanol added is between 8.0 to 10.0 times volume per gram of compound (II) preferably 10.0 times volume per gram of compound (II).

Butylated hydroxy toluene and butylated hydroxy anisole are added to the mixture. The amount of the anti-oxidant added is 0.005% weight/weight of compound (II).

The mixture is optionally treated with activated carbon and filtered. Water is added gradually to the filtrate. The volume of water added is between 13.0 and 15.0 times volume by weight of compound (II), but preferably 13.0 times volume/weight of compound (II). Water is added in 30-45 minutes at ambient temperature and stirred at 60-90 minutes for complete crystallization of compound (I). The mixture is filtered and washed with 25% aqueous methanol. The wet cake is dried at 40-45° C. under vacuum for 4.0 to 5.0 hours.

Simvastatin of formula (I) is obtained in an overall yield of between 82-86% with purity between 99.5% and 99.8% with dimer impurity (III) below 0.05% and anhydro impurity (IV) below 0.15%.

Compound (I) prepared by this method conforms to pharmacopoeial specifications.

The invention is further illustrated by the following non-limiting examples.

EXAMPLE 1

Preparation of 6(R)-[2-[8(S)-(2,2-dimethylbutyryloxy)-2(S),6(R)-dimethyl-1,2,6,7,8,8a(R)-hexahydro-1(S)-napthyl]ethyl]-4(R)-hydroxy-3,4,5,6-tetrahydro-2H-pyran-2-one (Simvastatin)

Ammonium-7-[1,2,6,7,8,8a (R-hexahydro-2(S), 6(R)-dimethyl-8(S)-(2,2-dimethylbutyryloxy)-1(S)-naphthyl]-3(R),5(R)-dihydroxyheptanoate (Simvastatin ammonium salt) (100 gms; 0.22 moles) is added to dichloromethane under a nitrogen atmosphere at 25-30° C. Orthophosphoric acid (38.17 gms; 0.33 moles) is added to the suspension and the mixture is heated under nitrogen atmosphere at 35±2° C. for 12-14 hours. The reaction mixture was cooled to 25-30° C., and 25% NaCl solution (250 ml) was added and the pH adjusted between 8.0 and 9.0 by addition of 25% ammonia solution. The organic layer was separated and concentrated under reduced pressure below 30° C. Cyclohexane (500 ml) was added and the mixture was concentrated under reduced pressure below 50° C. Cyclohexane (800 ml) was again added to the residue and stirred. Triethyl amine (22.3 gms; 0.22 moles) was added to the mixture and refluxed at 78±2° C. for 30-40 minutes. The mixture was cooled to 25-30° C., stirred for 60 minutes for complete crystallization of simvastatin (I) and filtered. The wet cake was washed with cyclohexane (100 ml) and dried at 40-45° C. for 60 minutes.

The partially dried simvastatin (I) was dissolved in methanol (1000 ml). Butylated hydroxy toluene (5 mgms) and butylated hydroxy anisole (5 mgms) were added to the mixture and after optional carbon treatment was filtered and cooled to 25-30° C. Water (1300 ml) was added gradually to the filtrate in 45 minutes at same temperature and cooled to 0-5° C. The mixture was agitated at same temperature for 90 minutes and filtered. The wet cake was washed with a (4:1) mixture of water:methanol (200 ml). The wet cake was dried at 40-45° C. Yield: 79.6 gms; % Yield: 86.3; Purity: 99.7%.

EXAMPLE 2

Preparation of 6(R)-[2-[8(S)-(2,2-dimethylbutyryloxy)-2(S),6(R)-dimethyl-1,2,6,7,8,8a(R)-hexahydro-[(S)-napthyl]ethyl]-4(R)-hydroxy-3,4,5,6-tetrahydro-2H-pyran-2-one (Simvastatin)

Ammonium-7-[1,2,6,7,8,8a(R-hexahydro-2(S), 6(R)-dimethyl-8(S)-(2,2-dimethylbutyryloxy)-1(S)-naphthyl]-3(R),5(R)-dihydroxyheptanoate (Simvastatin ammonium salt) (100 gms; 0.22 moles) is added to dichloromethane under a nitrogen atmosphere at 25-30° C. Orthophosphoric acid (63.17 gms; 0.55 moles) is added to the suspension and the mixture is heated under nitrogen atmosphere at 35±2° C. for 12-14 hours. The reaction mixture was cooled to 25-30° C., 25% NaCl solution (250 ml) was added and the pH adjusted between 8.0 and 9.0 by addition of 25% ammonia solution. The organic layer was separated and concentrated under reduced pressure below 30° C. Cyclohexane (500 ml) was added and the mixture was concentrated under reduced pressure below 50° C. Cyclohexane (800 ml) was again added to the residue and stirred. Triethyl amine (33.45 gms; 0.33 moles) was added to the mixture and refluxed at 78±2° C. for 30-40 minutes. The mixture was cooled to 25-30° C., stirred for 60 minutes for complete crystallization of simvastatin (I) and filtered. The wet cake was washed with cyclohexane (100 ml) and dried at 40-45° C. for 60 minutes.

The partially dried simvastatin (I) was dissolved in methanol (1000 ml). Butylated hydroxy toluene (5 mgms) and butylated hydroxy anisole (5 mgms) were added to the mixture and after optional carbon treatment was filtered and cooled to 25-30° C. Water (1300 ml) was added gradually to the filtrate in 45 minutes at same temperature and cooled to 0-5° C. The mixture was agitated at same temperature for 90 minutes and filtered. The wet cake was washed with a (4:1) mixture of water:methanol (200 ml). The wet cake was dried at 40-45° C. Yield: 78.9 gms; % Yield: 85.8; Purity: 99.8%.

EXAMPLE 3

Preparation of 6(R)-[2-[8(S)-(2,2-dimethylbutyryloxy)-2(S),6(R)-dimethyl-1,2,6,7,8,8a(R)-hexahydro-[(S)-napthyl]ethyl]-4(R)-hydroxy-3,4,5,6-tetrahydro-2H-pyran-2-one (Simvastatin)

Ammonium-7-[1,2,6,7,8,8a(R-hexahydro-2(S), 6(R)dimethyl-8(S)-(2,2-dimethylbutyryloxy)-1(S)-naphthyl]-3(R),5 (R)-dihydroxyheptanoate (Simvastatin ammonium salt) (100 gms; 0.22 moles) is added to dichloromethane under a nitrogen atmosphere at 25-30° C. Orthophosphoric acid (41.98 gms; 0.242 moles) is added to the suspension and the mixture is heated under nitrogen atmosphere at 35±2° C. for 12-14 hours. The reaction mixture was cooled to 25-30° C., 25% NaCl solution (250 ml) was added and the pH adjusted between 8.0 and 9.0 by addition of 25% ammonia solution. The organic layer was separated and concentrated under reduced pressure below 30° C. Cyclohexane (500 ml) was added and the mixture was concentrated under reduced pressure below 50° C. Cyclohexane (800 ml) was again added to the residue and stirred. Triethyl amine (22.3 gms; 0.22 moles) was added to the mixture and refluxed at 78±2° C. for 30-40 minutes. The mixture was cooled to 25-30° C., stirred for 60 minutes for complete crystallization of simvastatin (I) and filtered. The wet cake was washed with cyclohexane (100 ml) and dried at 40-45° C. for 60 minutes.

The partially dried simvastatin (I) was dissolved in methanol (1000 ml). Butylated hydroxy toluene (5 mgms) and butylated hydroxy anisole (5 mgms) were added to the mixture and after optional carbon treatment was filtered and cooled to 25-30° C. Water (1300 ml) was added gradually to the filtrate in 45 minutes at same temperature and cooled to 0-5° C. The mixture was agitated at same temperature for 90 minutes and filtered. The wet cake was washed with a (4:1) mixture of water:methanol (200 ml). The wet cake was dried at 40-45° C. Yield: 79.3 gms; % Yield: 86.1; Purity: 99.7%.

The invention claimed is:

1. A process for preparation of compound (I)

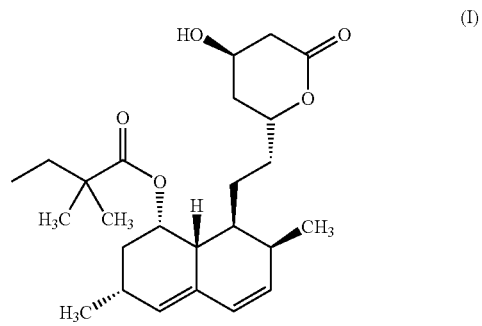

comprising agitating a compound of formula (II),

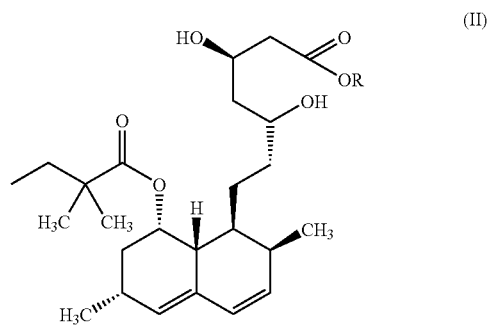

wherein R is $NH_4^+$ in dichloromethane, wherein the proportion of the solvent to substrate is between 17 and 20 times (w/w) per gram of compound (II), in an inert atmosphere at a temperature of between 27° C. to 40° C. in the presence of orthophosphoric acid, followed by neutralization with an inorganic base and obtaining compound of formula (I) in high purity and substantially free of impurities through isolation and crystallization.

2. A process according to claim 1, wherein the temperature is between 33° C. and 40° C.

3. A process according to claim 1, wherein orthophosphoric acid is employed in molar proportion of 1.0 mole to 2.5 mole per mole of compound (II).

4. A process according to claim 1, wherein the inorganic base is aqueous ammonia solution.

5. A process according to claim 1, wherein isolation comprises i) separating and evaporating the organic layer,
ii) adding a hydrophobic solvent to the residue and evaporating the solvent,
iii) dissolving the residue in a hydrophobic solvent, and adding an organic base to the mixture, and
iv) refluxing the mixture and cooling to ambient temperature followed by recovering compound of formula (I) by filtration.

6. A process according to claim 5, wherein the hydrophobic solvent is cyclohexane.

7. A process according to claim 5, wherein the organic base is triethyl amine.

8. A process according to claim 1, wherein crystallization comprises
  i) dissolving compound (I) in a water-miscible solvent,
  ii) adding water to the mixture followed by crystallization of compound (I) and cooling between 0° C. and 5° C., and
  iii) collecting the filtered compound (I) in high purity by filtration.

9. A process according to claim 8, wherein the water-miscible solvent is alkanol.

10. A process according to claim 9, wherein the alkanol is methanol.

* * * * *